US009326848B2

(12) United States Patent
Woods

(10) Patent No.: US 9,326,848 B2
(45) Date of Patent: May 3, 2016

(54) ACTUATOR FOR DEVICE FOR DELIVERY OF OPHTHALMIC LENSES

(71) Applicant: Duckworth and Kent Limited, Hertfordshire (GB)

(72) Inventor: Stephen Paul Woods, Hertfordshire (GB)

(73) Assignee: Duckworth and Kent Limited (GB)

( * ) Notice: Subject to any disclaimer, the term of this patent is extended or adjusted under 35 U.S.C. 154(b) by 0 days.

(21) Appl. No.: 13/859,784

(22) Filed: Apr. 10, 2013

(65) Prior Publication Data

US 2013/0274756 A1 Oct. 17, 2013

(30) Foreign Application Priority Data

Apr. 12, 2012 (GB) .................................. 1206480.4

(51) Int. Cl.
*A61F 2/16* (2006.01)
(52) U.S. Cl.
CPC .................................... *A61F 2/1672* (2013.01)
(58) Field of Classification Search
CPC .................................................... A61F 2/1672
USPC .................. 606/182, 166, 172, 107; 604/118, 604/59–64; 623/907, 6.12; 607/107
See application file for complete search history.

(56) References Cited

U.S. PATENT DOCUMENTS

| 1,078,502 | A | | 11/1913 | Hermann | |
|---|---|---|---|---|---|
| 4,724,837 | A | * | 2/1988 | Gannon | 606/166 |
| 4,744,790 | A | * | 5/1988 | Jankowski et al. | 604/232 |
| 5,582,598 | A | * | 12/1996 | Chanoch | 604/208 |
| 5,800,442 | A | | 9/1998 | Wolf et al. | |
| 6,059,791 | A | * | 5/2000 | Chambers | 606/107 |
| 6,267,768 | B1 | * | 7/2001 | Deacon et al. | 606/107 |
| 2004/0122359 | A1 | * | 6/2004 | Wenz et al. | 604/82 |
| 2004/0186484 | A1 | * | 9/2004 | Ryan | 606/107 |
| 2005/0192541 | A1 | * | 9/2005 | Novacek et al. | 604/195 |
| 2006/0229633 | A1 | | 10/2006 | Shepherd | |
| 2006/0235429 | A1 | * | 10/2006 | Lee et al. | 606/107 |
| 2009/0112223 | A1 | | 4/2009 | Downer et al. | |
| 2010/0217274 | A1 | * | 8/2010 | Lee et al. | 606/107 |
| 2011/0270264 | A1 | * | 11/2011 | Shoji et al. | 606/107 |
| 2012/0022548 | A1 | * | 1/2012 | Zacharias | 606/107 |
| 2013/0006259 | A1 | * | 1/2013 | Sanger | 606/107 |

FOREIGN PATENT DOCUMENTS

| EP | 1728488 | 12/2006 |
|---|---|---|
| GB | 2501109 | 10/2013 |
| JP | 2004/229977 | 8/2004 |
| WO | WO 2007/080868 | 7/2007 |
| WO | WO 2011/126144 A1 | 10/2011 |

* cited by examiner

*Primary Examiner* — Richard Louis
(74) *Attorney, Agent, or Firm* — Baker & Hostetler LLP

(57) ABSTRACT

The actuator comprises a barrel and a plunger received within the barrel. A clutch mechanism is operable between the plunger and the barrel. The clutch mechanism includes a driven member and a fixed member having respective castellations. The driven member carries pins which engage a three-start thread on the plunger. The castellations are urged into engagement by three annular springs. In the engaged condition of the clutch, the plunger is advanced by rotation relative to the barrel. An axial load on the plunger disengages the clutch mechanism, allowing the plunger to be advanced axially while rotating the driven member. Two-handed or one-handed operation according to a user's choice is therefore possible. The actuator can be used in combination with a lens delivery device.

23 Claims, 4 Drawing Sheets

ACTUATOR FOR DEVICE FOR DELIVERY OF OPHTHALMIC LENSES

CROSS-REFERENCE TO RELATED APPLICATION

This application claims priority from United Kingdom Application 1206480.4 filed 12 Apr. 2012.

BACKGROUND OF THE INVENTION

1. Field of the Invention

The present invention relates to the delivery of ophthalmic lenses.

2. Description of the Prior Art

Intraocular lenses are implanted into the eye through very small incisions in the eye, usually in the cornea, the lenses being rolled into a spiral or cylindrical shape prior to delivery.

Delivery can be carried out using a delivery device which is controlled manually by a surgeon, employing either a one-handed or a two-handed technique.

In many delivery devices substantial manual force can be required to progress the lens through the device. This can lead to difficulties for the surgeon as the procedure requires a great deal of control at the final stage of lens delivery, this often being as a result of the lens delivery device having a tapered cavity through which a rolled lens is progressed linearly prior to delivery into the eye, the degree of rolling of the lens being increased by the tapering of the cavity.

The lack of control at the final stage of delivery is an issue particularly associated with one-handed delivery techniques. These techniques usually involve delivery of a lens by depression of a plunger by the surgeon to progress the lens through the device and into the eye. This offers the advantage of freeing the surgeon's other hand for other actions.

An alternative is the two-handed technique of lens delivery. This usually involves delivery of a lens by rotation of a threaded plunger by the surgeon to produce linear motion in order to progress the lens through the device and into the eye. This technique offers the advantage of greater control of the delivery but with the disadvantage restricting the surgeon's freedom to perform other tasks using his other hand.

WO 2011/126144 A1 (Hoya Corporation) discloses an ocular implant insertion apparatus configured for screw-type and push-type operation. The apparatus has a body and a plunger, one of which has a helical slot and a longitudinal groove which intersects the slot. The other of the body and plunger has a protrusion which fits within the groove or the slot. The apparatus is switched between the two types of operation by visual alignment by the user of appropriate parts of the apparatus.

US 2009/0112223 A1 (Downer et al) discloses a lens delivery system handpiece having a threaded plunger rod with a ball lock ring. Locking the ring causes the plunger to be advanced by turning a thumbscrew or knob. Unlocking the ring allows the plunger to be advanced by pushing on the thumbscrew or knob in a manner similar to a syringe.

BRIEF SUMMARY OF THE INVENTION

The present invention provides an actuator for a device for delivery of ophthalmic lenses, the actuator comprising a barrel, a plunger receivable within the barrel and movable between a first, withdrawn position and a second, more advanced position, and a coupling means operable between the plunger and the barrel and operable selectively in a first condition to allow the plunger to move axially relative to the barrel from the first to the second position and in a second condition in which rotation of the plunger relative to the barrel produces axial movement of the plunger from the first position to the second position, the coupling means being responsive to an axial load on the plunger to change from the second to the first condition and from the first to the second condition on release of the load.

With such an actuator, the surgeon or other user can select between longitudinal or rotary plunger movement simply by adjusting the longitudinal manual load on the plunger. This allows the user a choice between employing a one-handed technique, when the coupling means is in its first condition, and a two-handed technique, when the coupling means is in its second condition, of lens delivery, or a combination of the two, during any particular lens insertion procedure.

Further, the user may maintain one-handed operation, even when resistance to plunger movement is encountered, simply by applying an axial load to the plunger, as can conveniently be done whilst holding the actuator in one hand.

The plunger may include means for coupling the linear movement of the plunger to a delivery device, the coupling means preferably being arranged to remove any rotational element of the motion of the plunger to produce a solely linear output.

Generally-speaking, the actuator preferably produces a linear output which may or may not also have a rotational component.

Advantageously, the first and the second conditions are attainable over the same portion of the axial movement of the plunger relative to the barrel.

Conveniently, the coupling means comprise a screw-threaded portion of the plunger.

Advantageously, the coupling means comprise a clutch mechanism operable between the plunger and the barrel, the plunger conveniently extending extends coaxially of the clutch mechanism.

Preferably, the clutch mechanism comprises relatively-movable first and second interengageable elements, one of which is fixed relative to the barrel and the other of which is moveable relative thereto, and resilient biasing means urging the clutch elements into engagement with each other.

The clutch elements may have respective sets of castellations which engage with each other in the engaged condition.

Conveniently, the plunger passes coaxially through the first and second clutch elements and has a screw-threaded portion which is engageable with one of the elements, whereby the plunger can move by rotation thereof from its first to its second position when the first and second elements are engaged.

Preferably, the plunger can move from its first to its second position by axial movement thereof when the first and second clutch elements are disengaged.

Advantageously, an axial load on the plunger produces relative movement of the clutch elements and thereby changes the coupling means from its second to its first condition.

When a screw thread is provided, the clutch element which is in engagement with the screw thread has one or more protruding pins or other follower elements engaging with the thread.

Preferably, the thread is a multi-start thread, for example a two- or three-start thread. The use of a multi-start thread can provide a large degree of advancement of the plunger per rotation in the second condition of the coupling means.

A multi-start thread also facilitates coupling of the protruding elements with the thread with the minimum amount of rotation of the plunger being required to achieve this.

Preferably, the plunger has a first, forward portion which does not engage with the coupling means and a second, rearward portion, preferably a threaded portion, which engages with the coupling means, whereby the plunger can move axially relative to the barrel over a first portion of its stroke without operation of the coupling means.

Advantageously, the groove(s) of the threaded portion are flared at the transition between the first and second portions.

Alternatively however it is possible for the threaded portion to be in engagement with coupling means throughout the stroke of movement of the plunger. Flaring of the entry points of the thread(s) is then not needed.

Preferably, the resilient biasing means of the clutch mechanism are operable between the movable clutch element and an annular carrier member through which the plunger extends.

The resilient biasing means conveniently comprise a plurality of resilient annular elements lying in planes lying parallel to the axis of the plunger.

In another arrangement, the resilient biasing means comprise a plurality of resilient elements extending axially between the carrier member and the movable clutch element which are conveniently formed integrally.

Actuators according to the invention can be supplied as separate parts for fitment to delivery devices of a wide range of types. Alternatively, delivery devices can incorporate an actuator according to the invention as a part of the delivery device.

Actuators according to the invention are preferably linear actuators, or actuators producing a combined linear and rotational output movement.

BRIEF DESCRIPTION OF THE DRAWINGS

Embodiments of the invention will now be described by way of example with reference to the drawings of this specification, in which.

DETAILED DESCRIPTION

Figure 1:
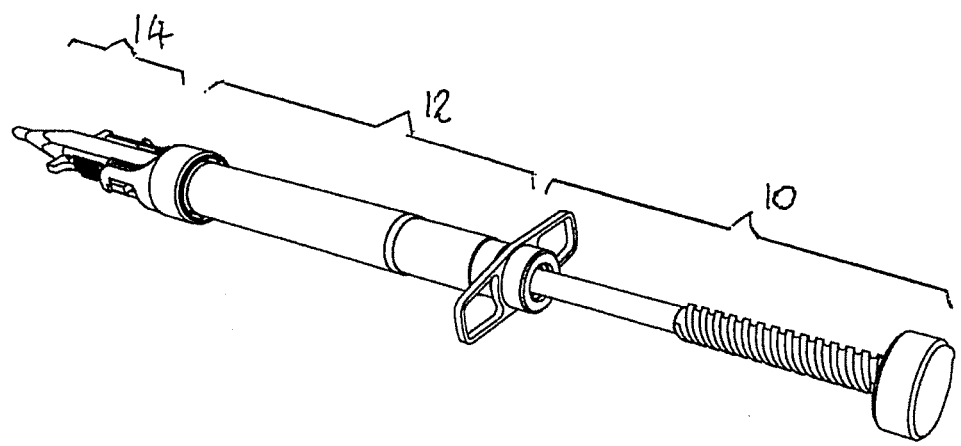
FIG. 1 is a perspective view of an assembly of a delivery device for ophthalmic lenses and an actuator which is an embodiment of the present invention.

FIG. 1 of the drawings shows an actuator indicated generally at 10 fitted to a delivery device 12 of known type. The delivery device is fitted at its forward end with a lens cartridge 14, also of known type, which contains a rolled or folded lens located in a tapering cavity. The lens is delivered to a patient's eye through an opening in the tip of the cartridge 14.

Figure 2:
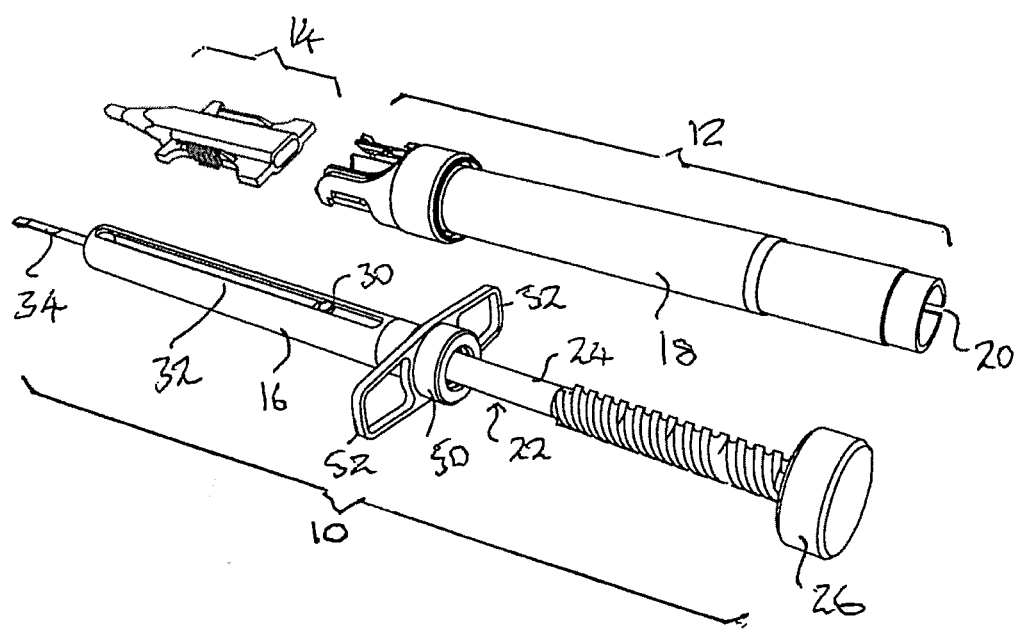
FIG. 2 corresponds to FIG. 1 but shows the delivery device and actuator disassembled.

FIG. 2 shows the assembly of FIG. 1 with the actuator disassembled from the delivery device 12 and the lens cartridge 14 dismounted from the delivery device. It will also be seen from FIG. 2 that the actuator 10 comprises a barrel 16 which fits inside a sleeve 18 of the delivery device 12, the barrel 16 and sleeve 18 being secured together by a bayonet connection consisting of a slot 20 in the sleeve 18 and a pin (not visible in the drawings) on the barrel 16.

Figure 3:
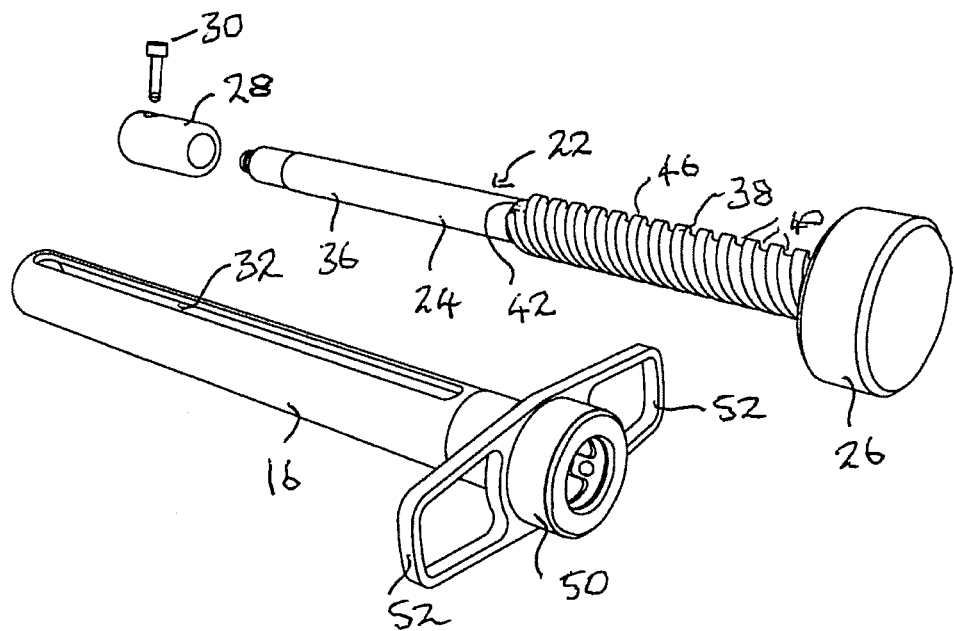
FIG. 3 corresponds to FIG. 2 but shows only the actuator.

FIGS. 2 and 3 of the drawings also show that the actuator 10 comprises a plunger 22 which is slidable in the barrel 16.

The plunger 22 (shown in more detail in FIG. 3) comprises a stem 24 which terminates at its rearward end in a cylindrical head 26. The stem 24 terminates at its forward end in a bush 28 which is a sliding fit in the interior bore of the barrel 16. The bush 28 is made from a suitable plastics material such as a polyetherketone (PEEK) and is freely rotatable on the stem 24 and carries a pin 30 which is received in a longitudinal slot 32 in the barrel 16 to constrain the bush against rotational movement relative to the barrel. A delivery needle 34 is mounted at its rearward end on the bush 28, the needle being shaped to be received in the lens cartridge 14 in order to make contact with a folded or rolled lens and to deliver the lens from the cartridge into a patient's eye as the needle is moved forwards as a result of forward movement of the plunger 22 in the barrel 16.

Figure 5:
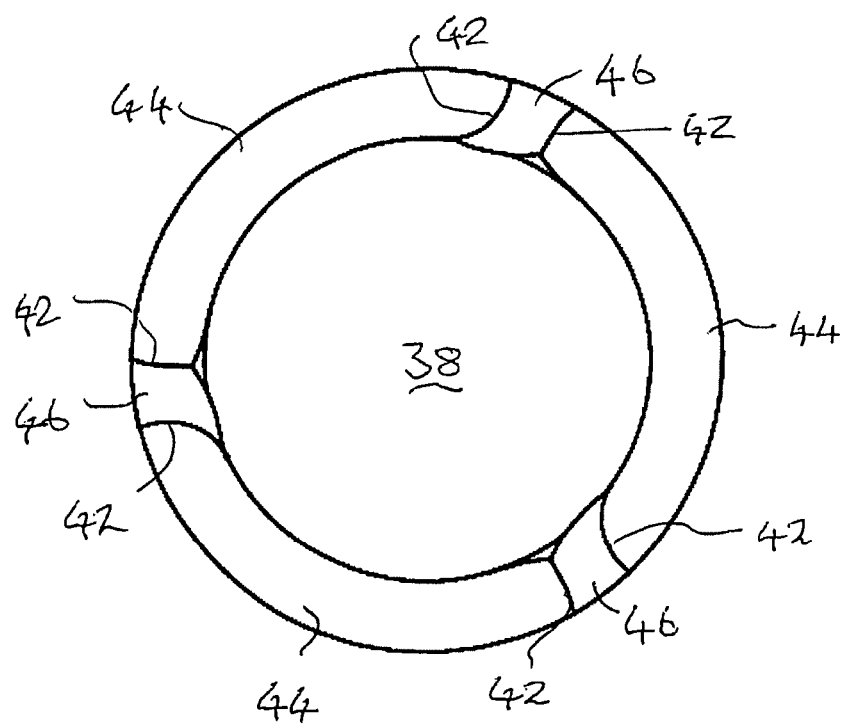
FIG. 5 is a cross-section on the line V-V on FIG. 4.

The stem 24 of the plunger 22 has a plain forward portion 36 and a threaded rearward portion 38 which has a three-start thread formed by three helical grooves 40 of U-shaped transverse section. For reasons which will become evident hereinafter, the grooves 40 widen at their open, forward ends into flared portions 42 which terminate in respective circumferential openings 44 which extend over arcs of about 100 degrees between rounded ends of the inter-groove ridges 46 which extend over arcs of about 20 degrees, as will be evident from FIG. 5 of the drawings.

The barrel 16 terminates at its rearward end in a cylindrical cup 50, just forwardly of which a pair of outwardly-extending ears 52 protrude one to each side. The ears 52 allow the actuator to be held in one hand by a user with the user's first and second fingers behind the ears and the user's thumb resting on the head 26 of the plunger 22.

The cup 50 receives a clutch mechanism 54 which is operative to provide coupling between the plunger 22 and the barrel 16 of the actuator 10. The clutch mechanism 54 is arranged coaxially around the plunger 22, as can be best seen in FIG. 4 of the drawings which also shows the rearward end of the barrel 16 and a portion of the plunger 22.

The clutch mechanism 54 includes a PTFE friction-reducing washer 56, an annular support member 58, an annular driven member 60 and an end cap 62 which is a press-fit in the rearward end of the cup 50 and is secured against rotation relative thereto. The stem 24 of the plunger 22 extends coaxially through the washer 56, support member 58, driven member 60 and end cap 62.

The annular support member 58 is formed with three circumferential turrets 64, each extending over an arc of approximately 90 degrees. Three arcuate gaps 66 each extending over arcs of about 30 degrees lie between the turrets 64. Each turret 64 has in it a recess 68 of elongate transverse section. A resilient biasing member 70, such as a clutch spring, is seated in each recess 68, each resilient biasing member 70 consisting of a rectangular-section ring of resilient plastics material. The resilient biasing members 70 are circular in plan when in a relaxed condition but can be resiliently deformed to be oval in plan. Springs of this type have been found to be particularly simple to form and their rates readily determined and controlled.

The resilient biasing members 70 act on a forward annular face 72 of the driven member 60 and therefore act to bias the support 58 and the driven member 60 apart in the axial direction.

Figure 6:
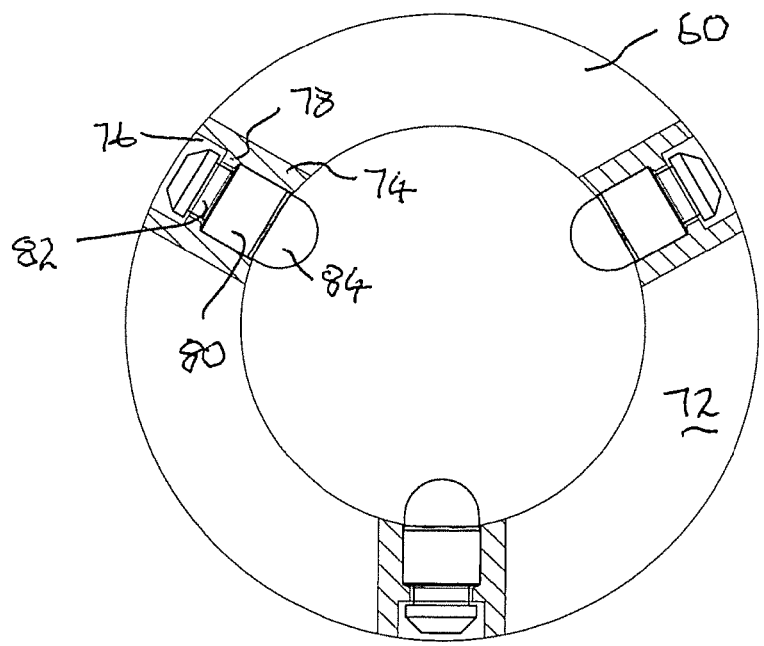
FIG. 6 is a cross-section on the line VI-VI on FIG. 4.

The driven member 60 is formed on its forward face 72 with three equidistantly-spaced turrets 74, each extending over an arc of approximately 30 degrees, as will be seen most clearly in FIG. 6 of the drawings. The turrets 74 of the driven member are received in the gaps 66 between the turrets 64 of the support member 58. As can be seen from FIG. 6, each turret 74 has a radial bore 76 having an internal circumferential ridge 78. Each bore 76 receives a respective drive pin 80 which has a circumferential groove 82 which is a snap-fit over the corresponding ridge 78 in the respective bore 76. Each pin 80 has a hemispherical inner end 84 which projects radially inwardly from the driven member 60.

The driven member 60 is formed on its rearward annular face with a series of castellations 86 which engage a series of corresponding castellations 88 formed on the forward face of the end cap 62. The resilient biasing members 70 therefore bias the series of castellations 86, 88 into engagement with each other and lock the driven member 60 and end cap 62 together against relative rotational movement. The axial length of the cup 50 is chosen such that the resilient biasing members 70 are slightly deformed from their circular shapes in this condition of the clutch mechanism, thus providing a small preloading force.

The hemispherical end portions 84 of the pins 80 which protrude radially inwardly are positioned so as to be received in a respective one of the grooves 40 formed by the threads of the threaded portion 38 of the plunger 24, entry of the pins into the grooves being facilitated by the flared end portions 42 of the grooves 40.

The support member 58, resilient biasing members 70 and pins 80 are formed from a suitable engineering plastics material such as a polyetherketone (PEEK). The driven member 60 is formed from a polyetherimide such as that sold under the name ULTEM®. Except as specifically mentioned otherwise, the actuator is made from a suitable titanium alloy. Stainless steel could be used instead.

The clutch mechanism operates as follows. In the disengaged condition of the mechanism already referred to, the driven member 60 is urged by the resilient biasing members 70 rearwardly relative to the end cap 62. The castellations 86, 88 are thereby brought into engagement and the driven member 60 and the support member 58 are locked against rotation relative to the end cap 62. In this condition of the clutch, the forward, plain portion 36 of the plunger 24 can pass unimpeded through the clutch mechanism and the plunger 24 can be advanced correspondingly axially of the barrel 16.

If the plunger 24 is advanced through the barrel to an extent that its threaded portion 38 passes into the clutch mechanism, the pins 80 engage in respective grooves 40 of the threaded portion 38. Whilst the clutch mechanism remains engaged, the plunger 22 can be advanced further through the barrel 16 if it is rotated to allow the pins 80 to pass helically along the grooves 40 of the thread. This is achieved in the absence of any significant axial load on the plunger 22.

If however a significant axial load is placed on the plunger 22, the pins 80, rather than passing helically along the grooves 40, engage with the walls of the grooves with the result that the load on the plunger 22 is transferred to the driven member 60 which is shifted axially against the bias of the resilient biasing members 70 such that the castellations 86, 88 disengage to allow the driven member 60 to rotate relative to the end cap 62. The plunger 22 can now be advanced forwardly relative to the barrel 16 for so long as the axial load is maintained.

Figure 7:
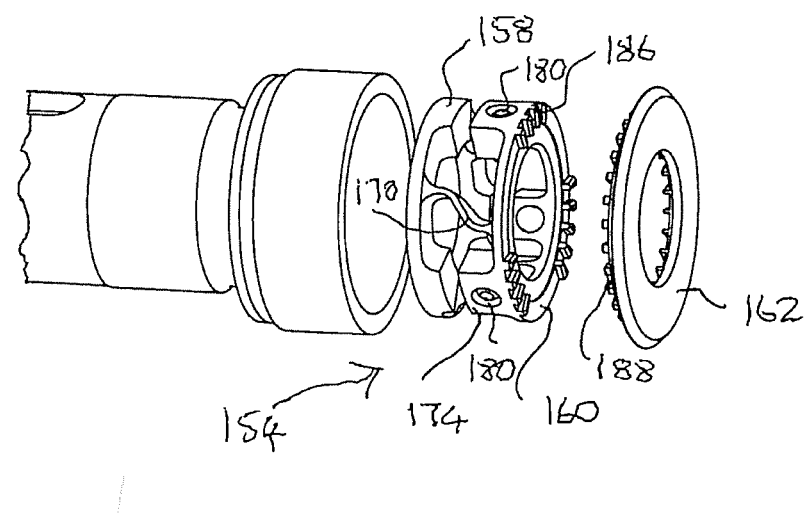
FIG. 7 is an exploded perspective view of a modified clutch mechanism.

FIG. 7 shows a modified clutch mechanism, the parts of which corresponding to parts of the mechanism 54 are indicated by reference numerals increased by "100" compared with the reference numerals used for the parts of the mechanism 54.

The modified clutch mechanism 154 comprises a support member 158 and a driven member 160 which are formed integrally as a plastics moulding and which are joined by integral resilient biasing members 170, such as resilient twisted straps, corresponding to the resilient biasing members 70. The driven member 160 has three circumferentially-spaced turrets 174 which support drive pins 180 in a manner corresponding exactly to that described hereinbefore for the clutch mechanism 54. The rearward face of the driven member 160 is formed with castellations 186 which engage with castellations 188 on the forward face of the end cap 162.

The modified clutch mechanism operates in a very similar manner to the mechanism 54, except that the resilient loading is provided by the resilient biasing members 170 and not the resilient biasing members 70.

The use of the actuators shown in FIGS. 1 to 6 and FIG. 7 in connection with a delivery device for the insertion of a rolled ophthalmic lens into the human eye will now be described.

Figure 4:
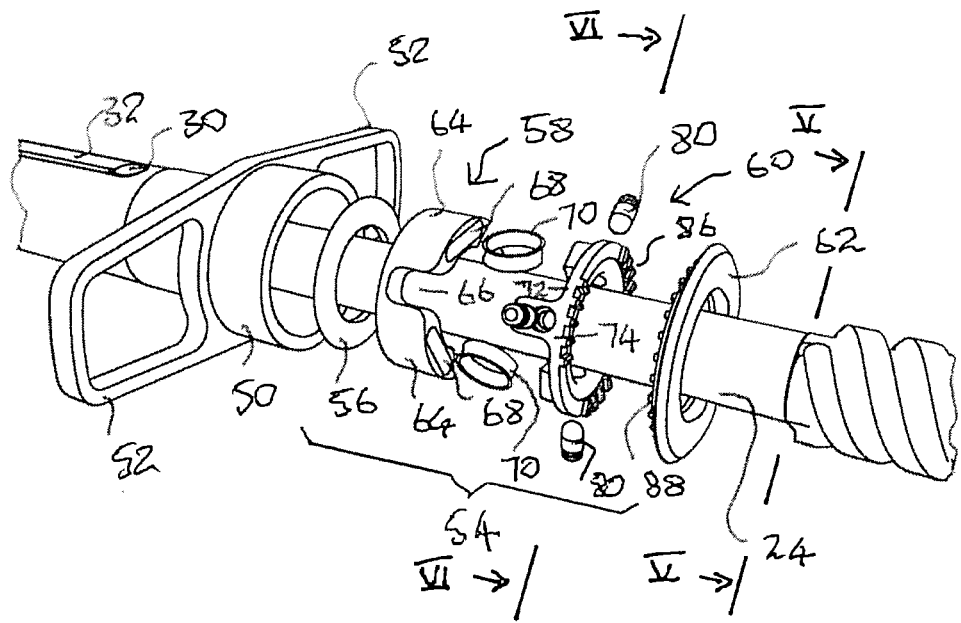
FIG. 4 is an exploded perspective view of a clutch mechanism of the actuator of FIG. 3.

An actuator having a clutch mechanism 54 as shown in FIG. 4 or a clutch mechanism 154 as shown in FIG. 7 is assembled to a delivery device 12 as shown in FIGS. 1 and 2, the delivery device being fitted with a lens cartridge 14 as also shown in FIGS. 1 and 2. Advancement of the plunger 22 of the actuator 10 through the barrel 16 of the actuator causes the delivery needle 34 to pass into the lens cartridge 14 with the result that the rolled ophthalmic lens contained in the cartridge 14 is delivered outwardly through the aperture in the tip of the cartridge 14.

During the first portion of the stroke of movement of the plunger 22, the plain, unthreaded forward portion 36 of the stem 24 of the plunger 22 passes through the clutch mechanism 54 or 154 without contact, allowing the delivery needle 34 to be advanced rapidly and with little resistance, as is desirable during the initial phase of lens delivery before the tip of the needle 34 contacts the rolled lens in the cartridge 14. During this initial phase, the surgeon may hold the delivery device and actuator with his first and second fingers behind the ears 52 and his thumb on the head 26.

In the next phase of the delivery process, the threaded portion 38 of the plunger stem 24 engages with the clutch mechanism 54 or 154 as described above. The surgeon now has the option as he wishes either to continue the forward movement of the plunger in the actuator barrel in a one-handed operation which results in an axial loading on the plunger 22 with the effect that the clutch mechanism 54 or 154 disengages and the plunger can continued to be moved forwardly through the delivery device. Alternatively, if he wishes, the surgeon can continue to hold the barrel 16 of the actuator in one hand and then, by twisting the head 26 of the plunger 22 advance the needle to deliver the lens from the cartridge 14. In this case, in the absence of substantial axial loading on the plunger, the clutch 54 or 154 remains engaged and the twisting movement of the plunger stem 24 results in further forward movement of the plunger with the pins 80 or 180 of the clutch mechanism 54 or 154 engaged in the grooves 40 of the threaded portion of the plunger stem. This allows the surgeon, according to his choice, to control the second stage of the insertion operation in a two-handed operation involving a rotary motion of the plunger 22 relative to the barrel 16. The particularly advantageous feature of allowing the surgeon at his choice to employ a one-handed or a two-handed technique of lens delivery is therefore provided by the actuator of the present invention.

What is claimed is:
1. An actuator for a device for delivery of ophthalmic lenses, the actuator comprising:
   a barrel,
   a plunger receivable within the barrel and movable in an axial direction between a first, withdrawn position and a second, more advanced position, a coupling operable between the plunger and the barrel and operable selectively in a first condition and a second condition, wherein in the first condition the coupling is configured to allow the plunger to move in the axial direction relative to the barrel from the first position to the second position when an axial load is applied to the plunger in the axial direction, and wherein in the second condition the coupling is configured to allow the plunger to move in the axial direction relative to the barrel from the first position to the second position when the plunger is rotated relative to the barrel, and a resilient biasing member which biases the coupling into its second condition, the coupling being responsive to the axial load on the plunger opposing the bias of the resilient biasing member to change from the second to the first condition and from the first to the second condition on release of the axial load.

2. An actuator according to claim 1, in which the first and the second conditions are attainable over the same portion of the axial movement of the plunger relative to the barrel.

3. An actuator according to claim 1, in which, in the first condition, the screw-threaded portion is disengaged from the barrel, and in the second condition, the screw-threaded portion is engaged with the barrel.

4. An actuator according to claim 1, in which, in the first condition, the thread follower portion is disengaged from the barrel, and in the second condition, the thread follower portion is engaged with the barrel.

5. An actuator according to claim 1, in which the plunger extends coaxially with the coupling.

6. An actuator according to claim 1, in which the coupling comprises first and second interengageable elements that are moveable relative to one another, one of which is fixed relative to the barrel and the other of which is moveable relative thereto, and the resilient biasing member urges the first and second interengageable elements into engagement with each other.

7. An actuator according to claim 6, in which the first and second interengageable elements have respective sets of castellations that engage with each other in the second condition.

8. An actuator according to claim 6, in which the plunger passes coaxially through the first and second interengageable elements and the screw-threaded portion is disposed on the plunger, the screw-threaded portion being engageable with one of the interengageable elements, whereby the plunger can move by rotation thereof from its first to its second position when the first and second interengageable elements are engaged.

9. An actuator according to claim 8, in which the plunger can move from its first to its second position by axial movement thereof when the first and second interengageable elements are disengaged from each other.

10. An actuator according to claim 8, in which an axial load on the plunger produces relative movement of the first and second interengageable elements and thereby changes the coupling from its second to its first condition.

11. An actuator according to claim 8, in which one of the first and second interengageable elements that is in engagement with the screw thread comprises the thread follower portion which includes one or more protruding elements.

12. An actuator according to claim 8, in which the screw-threaded portion is a multi-start thread.

13. An actuator according to claim 8, in which the resilient biasing member is operable between the first and second interengageable elements and an annular support member through which the plunger extends.

14. An actuator according to claim 13, in which the resilient biasing member comprises a plurality of resilient annular elements each lying in a respective plane that is parallel to and offset from the longitudinal axis of the plunger.

15. An actuator according to claim 13, in which the resilient biasing member comprises a plurality of resilient elements extending axially between the carrier support member and the first and second interengageable elements.

16. An actuator according to claim 15, in which the plurality of resilient elements, the support member, and the first and second interengageable elements are formed integrally.

17. An actuator according to claim 1, in which the plunger has a first, forward portion which does not engage with the coupling and a second, rearward portion which engages with the coupling, whereby the plunger can move axially relative to the barrel over a first portion of its stroke without operation of the coupling.

18. An actuator according to claim 17, in which the second, rearward portion is a said screw-threaded portion.

19. An actuator according to claim 18, in which groove(s) of the screw-threaded portion are flared at a transition between the first and second portions.

20. An actuator according to claim 1, in which the screw-threaded portion is in engagement with the coupling throughout the stroke of movement of the plunger.

21. An actuator according to claim 1, in which the plunger has a delivery device coupling for coupling linear movement of the plunger to a delivery device.

22. An actuator according to claim 21, in which the delivery device coupling is arranged to produce a linear output movement having no rotational component.

23. A device for delivery of an ophthalmic lens, the device including an actuator according to claim 1.

* * * * *